United States Patent
Dingeldein et al.

(10) Patent No.: US 10,010,652 B2
(45) Date of Patent: Jul. 3, 2018

(54) PEO COATING ON MG SCREWS

(71) Applicant: AAP IMPLANTATE AG, Berlin (DE)

(72) Inventors: Elvira Dingeldein, Münchberg (DE); Cyrille Gasqueres, Aschaffenburg (DE); Amir Eliezer, Omer (IL); Marco Wolfstadter, Worth/Main (DE); Lydia Heimann, Hoesbach (DE)

(73) Assignee: AAP INPLANTATE AG, Berlin (DE)

( * ) Notice: Subject to any disclaimer, the term of this patent is extended or adjusted under 35 U.S.C. 154(b) by 70 days.

(21) Appl. No.: 15/010,583

(22) Filed: Jan. 29, 2016

(65) Prior Publication Data

US 2016/0144080 A1    May 26, 2016

Related U.S. Application Data

(62) Division of application No. 13/183,864, filed on Jul. 15, 2011, now Pat. No. 9,297,090.

(Continued)

(51) Int. Cl.
  *A61L 31/08*    (2006.01)
  *A61L 31/02*    (2006.01)
  (Continued)

(52) U.S. Cl.
  CPC .......... *A61L 31/086* (2013.01); *A61L 31/022* (2013.01); *A61L 31/148* (2013.01);
  (Continued)

(58) Field of Classification Search
  CPC . A61F 2/28; A61L 31/08; A61L 31/02; C25D 11/02; C25D 11/30; A61C 8/00
  See application file for complete search history.

(56) References Cited

U.S. PATENT DOCUMENTS

| 4,085,010 A | 4/1978 | Ishimori et al. |
| 4,172,771 A | 10/1979 | Grunke |

(Continued)

FOREIGN PATENT DOCUMENTS

| CN | 101054708 | 10/2007 |
| DE | 4303575 | 4/1994 |

(Continued)

OTHER PUBLICATIONS

Song, et al., "Electrodeposition of Ca-P Coatings on Biodegradable Mg Alloy: In Vitro Biomineralization Behavior", Acta Biomaterialia, 2010, pp. 1736-1742, 6.

(Continued)

*Primary Examiner* — Yashita Sharma
(74) *Attorney, Agent, or Firm* — Pearl Cohen Zedek Latzer Baratz LLP

(57) ABSTRACT

The present invention relates generally to a bio-degradable implant based on magnesium having a reduced corrosion rate and to a method for the production of such an implant. It is a method for treating a surface of a bio-degradable metallic implant comprising the following steps: providing a dispersed system comprising a colloid-dispersed apatite and adding an apatite powder to the dispersed system, subjecting an implant to the dispersed system such that a surface of the implant which is to be treated is immersed in the dispersed system wherein the implant comprises a magnesium based alloy, applying an AC voltage difference between the implant as a first electrode and a second electrode positioned in the dispersed system for generating a plasma electrolytic oxidation on the immersed surface of the implant so that the immersed surface is converted to an oxide film which is at least partially covered by apatites formed by the colloid-dispersed apatite and the apatite (Continued)

powder. The evolution of corrosion induced hydrogen gas evolution is decreased and osseointegration is improved.

15 Claims, 14 Drawing Sheets

Related U.S. Application Data

(60) Provisional application No. 61/364,970, filed on Jul. 16, 2010.

(51) Int. Cl.
*A61L 31/14* (2006.01)
*C25D 11/02* (2006.01)
*C25D 11/30* (2006.01)

(52) U.S. Cl.
CPC ............ *C25D 11/026* (2013.01); *C25D 11/30* (2013.01); *A61L 2400/18* (2013.01); *A61L 2420/02* (2013.01); *C25D 11/024* (2013.01)

(56) References Cited

U.S. PATENT DOCUMENTS

| | | | |
|---|---|---|---|
| 4,411,742 A | 10/1983 | Donakowski et al. | |
| 4,560,666 A | 12/1985 | Yoshida et al. | |
| 6,254,855 B1 | 7/2001 | Rudin et al. | |
| 2005/0079088 A1 | 4/2005 | Wirth et al. | |
| 2005/0221259 A1 | 10/2005 | Anderson | |
| 2006/0024250 A1 | 2/2006 | Powers et al. | |
| 2006/0089715 A1 | 4/2006 | Truckai et al. | |
| 2007/0003634 A1 | 1/2007 | Gibson et al. | |
| 2008/0086195 A1 | 4/2008 | Atanasoka et al. | |
| 2009/0130226 A1 | 5/2009 | Sung et al. | |
| 2009/0192628 A1 | 7/2009 | Ito et al. | |
| 2010/0131052 A1* | 5/2010 | Kappelt ................ A61L 31/022 623/1.46 |
| 2010/0305684 A1 | 12/2010 | Kim et al. | |

FOREIGN PATENT DOCUMENTS

| | | |
|---|---|---|
| DE | 102009023459 A1 | 12/2010 |
| EP | 1 231 299 | 8/2002 |
| EP | 2 233 162 | 9/2010 |
| WO | WO 2003/094774 | 11/2003 |
| WO | WO 2006/024125 | 3/2006 |
| WO | WO 2009/053670 | 4/2009 |
| WO | WO 2010/139451 | 12/2010 |

OTHER PUBLICATIONS

German Office Action Issued for DE 10 2010 027 532.8, dated Mar. 7, 2011, with English translation.
N. Hort et al., "Magnesium Alloys as Implant Materials—Principles of Property Design for Mg-RE Alloys", Acta Biomaterialia, vol. 6, Issue 5, pp. 1714-1725, May 2010.
Office Action from Chinese Patent Application No. 201180034745.4 dated Mar. 4, 2014.
Bard, Allen J. And Faulkner, Larry R., Electrochemical Methods Fundamental and Applications, 2001, pp. 18-24, Second Edition, John Wiley & Sons, Inc., NY, NY, USA.
European Office Action for Appl. No. 11748888.2 dated Jan. 1, 2016.

* cited by examiner

PEO COATING ON MG SCREWS

This application is a divisional application of U.S. application Ser. No. 13/183,864, filed Jul. 15, 2011, which claims the benefit of U.S. Provisional Application No. 61/364,970 filed Jul. 16, 2010, the contents of all of which are incorporated herein in their entirety.

DESCRIPTION

Field of the Invention

The present invention relates generally to a bio-degradable implant based on magnesium having a reduced degradation rate and to a method for the production of such an implant.

Background of the Invention

It is known that magnesium based alloys posses a number of advantages that make them of interest when considering for instance surgical implants. Of particular interest of such magnesium based implants is the possibility of using them to act both as a scaffolding structure on which new bone or tissue can grow and as a fixture structure to hold together a bone or a ligament long enough to allow natural healing to take place.

Magnesium and its alloys are of particular interest in this type of applications as they are bio-compatible and as they have a modulus of elasticity closer to bone than currently used materials. Another major advantage of using magnesium and its alloys as implant materials, for instance for the fabrication of surgical implants, are their ability to bio-degrade in situ. This in turn means that the implant does not remain in the body. A further surgery to remove the implant is not required.

However, recent animal implantation studies seem to exhibit sometimes only a partial direct bone contact of a magnesium based alloy after a certain time if implantation. A fibrous tissue layer separates the newly grown bone from the implant. Additionally, hydrogen gas formation and sometimes even gas bubbles seem to be present on the surface of the implant and in the surrounding tissue after 6 to 12 weeks of implantation. Hydrogen gas evolution or release occurs during the bio-degradation process. The volume of evolved or released hydrogen gas is related to the dissolution of the magnesium. Without being restricted to a theory it is believed that all of these problems are mainly or essentially due to a too fast initial degradation process of the magnesium implant in-vivo. The degradation rate of the magnesium based alloys seems to be too fast, in particular at the beginning directly after implantation. More hydrogen gas is generated than can be readily resorbed or absorbed by the surrounding tissue. This results in the formation of gas bubbles or gas pockets, for instance subcutaneous gas bubbles and/or gas bubbles in the soft-tissue, which could damage the surrounding tissue. This is the major drawback of magnesium and actually hampers the broad application of magnesium based implants.

A recent approach bases on a magnesium based alloy having an adapted composition and morphology. One specific alloy is designed. The composition and the morphology are adapted or designed such that hydrogen gas evolution is avoided (see for instance N. Hort et al., Acta Biomaterialia, Volume 6, Issue 5, Pages 1714-1725, May 2010: "Magnesium Alloys as Implant Materials—Principles of Property Design for Mg-RE Alloys").

On one hand the design of such an alloy is time-consuming and therefore expensive. On the other hand such a specific alloy possesses only one specific degradation rate. However, in general the degradation rate is dependent on the place of implantation in the body or on the purpose of the implant. For instance, the degradation times of an implant acting as a fixture to hold together a bone long enough to allow natural healing to take place and of an implant embodied as a screw to fix a ligament to a cartilage can be different.

Accordingly, it is an object of the present invention to provide a preferably bio-degradable implant of advanced properties, for instance of enhanced bio-compatibility and/or for providing improved implant-tissue-contact.

A bio-degradable implant should have a reduced degradation rate compared to untreated implants. Particularly, the degradation rate, in particular the initial degradation rate, should be reduced such that a gas accumulation in the tissue is at least reduced or avoided.

In particular it should be possible to control or to adapt the degradation rate or the bio-degradability of such an implant.

Preferably the ingrowth of human tissue and/or bone should be promoted by such an implant.

The fabrication of such an implant should be based on an easy and cost reduced concept.

SUMMARY OF THE INVENTION

The inventive solution of the object is surprisingly achieved by each of the subject matter of the respective attached independent claims.

Advantageous and/or preferred embodiments or refinements are the subject matter of the respective attached dependent claims.

The concept of the present invention generally bases on applying a coating onto an implant of a bio-degradable material wherein the coating is formed by an especially adapted plasma electrolytic oxidation (PEO), in particular having an especially adapted dispersed system. Such a PEO-coating, in particular in combination with a deposited or constituted apatite, preferably hydroxyl-apatite, enhances bio-compatibility and/or decreases the degradation rate or slows-down degradation. The formation of a coating enables a flexible adaptation of the degradation time of such a bio-degradable implant. The evolution or release of hydrogen gas, in particular the initial evolution of hydrogen gas, is decreased. Such a coating, in particular in combination with an apatite, preferably hydroxyl-apatite, also improves osseointegration.

Accordingly, the invention proposes a method for treating a surface of a, preferably bio-degradable, metallic implant comprising the following steps:

providing a dispersed system comprising a colloid-dispersed apatite and adding an apatite powder to the dispersed system or providing an apatite powder in the dispersed system, subjecting an implant, preferably a metallic implant, to the dispersed system such that a surface of the implant which is to be treated is immersed in the dispersed system, preferably wherein the implant comprises or is a magnesium based alloy, applying an AC voltage difference between the implant as a first electrode and/or a second electrode positioned in the dispersed system for generating a plasma electrolytic oxidation on the immersed surface of the implant so that the immersed surface is converted to an oxide film, in particular of the magnesium based alloy, which is at least partially covered by apatites which are, in particular at least partially, formed or constituted by the apatite powder and preferably the colloid-dispersed apatite.

The above mentioned method for treating a surface of a bio-degradable metallic implant also can be called as a method for adapting or for controlling the bio-degradability of a bio-degradable metallic implant or as a method for enhancing or controlling the degradation resistance of a bio-degradable metallic implant.

The invention also proposes an implant comprising a metal, preferably a biodegradable magnesium based alloy, having a treated surface wherein
  the treated surface is at least partially converted to an oxide film by plasma electrolytic oxidation using a dispersed system comprising a colloid-dispersed apatite and an apatite powder and wherein
  the converted surface is partially covered by apatites originating, in particular at least, from the apatite powder and preferably the colloid-dispersed apatite.

The colloid-dispersed apatite and the components of the apatite powder are deposited on the converted surface of the implant and/or at least partially form an apatite covering on the converted surface of the implant. The converted surface of the implant can be completely covered by the apatite covering. In dependence on the desired implant properties the apatite covering can form island-like and/or coral-like structures and/or clusters and/or a continuous or essentially continuous layer or coating on the converted surface of the implant. The implant according to the invention is characterized by an adapted or controlled or controllable degradation or degradation rate.

A porous oxide film or layer is grown by the plasma electrolytic oxidation (PEO) process. By the PEO process, the metallic substrate is provided as the first electrode, preferably as an anode, in an "electrolytic cell". Its surface is converted into the corresponding metal oxide under the applied electrical field. The oxide film consists of crystalline phases, with a highly porous surface and with components derived from both the dispersed system and the implant as a substrate. It is provided a synthesis of a metal-oxide-apatite-nanocomposite-coating by in situ deposition. The apatites are or the apatite is applied or deposited onto and/or constituted on the surface of the implant when oxidizing the implant surface. The present invention enables the formation of a coating onto any type of shape of an implant.

The colloid-dispersed system also can be called dispersion. It is a liquid containing dispersed particles, in detail containing the colloid-dispersed apatite and the apatite powder respectively its components.

Since the colloid-dispersed apatite owns a size in the nm-order, the size measurement in these dimensions is quite challenging. However, in general the colloid-dispersed apatite is expected to be provided, in particular at least partially, with an average size of about equal or less than 100 nm. The colloid-dispersed apatite generally has an elongated structure (for instance see FIG. 1e). In one embodiment the average length is ranging up to 100 nm. The size measurement bases on STEM (Scanning Transmission Electron Microscopy). It is emphasized that the size or the size distribution of the colloid-dispersed apatite essentially also depends on particle agglomeration. Therefore, to get the colloid-dispersed apatite in a non-agglomerated state, possible agglomerated particles have to be separated or an agglomeration has to be "destroyed". Accordingly, a separation process or deagglomeration has to be induced before the size measurement, for instance by means of an ultrasonic device.

The combination of the colloid-dispersed apatite and the apatite powder is essential for the formation of apatite clusters or an apatite covering on the converted implant surface. Without being restricted to a theory the following explanation is assumed:

The colloid-dispersed apatite represents small apatite particles, in particular with respect to the average size of the apatite powder. The colloid-dispersed apatite seems or its components seem to be too small for the formation of an apatite covering. It seems to be more likely that the colloid-dispersed apatite particles are destroyed in the intentionally generated plasma discharge of the PEO.

Since a powder generally owns a broad size distribution the apatite powder contains also large apatite particles. The size distribution of the apatite powder depends on and/or can be adjusted by its fabrication process (as explained in the subsequent description). A possible apatite powder distribution is provided with an average size ranging from 10 µm to 100 µm. The size measurement bases on LPS-analysis (Laser Particle Spectrometer). This enables the formation of an apatite covering on the oxide film of the converted implant surface. However, surprisingly the experimental results show that the application of the apatite powder in the dispersed system only, results to a coating with a clearly reduced or even no apatite covering. It is believed large particles alone are not able to stick on or to be deposited onto the oxide film of the converted implant surface.

The colloid-dispersed apatite seems to act as a kind of bonding agent or sacrificial apatite which promotes the deposition and/or bonding of larger sized apatite powder particles and/or the constitution of an apatite coating on the oxide film of the converted surface. The apatite powder alone does not seem to contain a sufficient amount of small apatite particles, even if the drying process and/or the milling process seem to be adjusted accordingly. In a further alternative and/or supplementary assumption the particles of the apatite powder seem to be not in an appropriate state.

The combination of the colloid-dispersed apatite and the apatite powder, in particular each having the above shown respective possible size distribution, enables the formation of a quite uniform and/or continuous apatite or non-continuous apatite distribution and/or apatite covering or layer.

The colloid-dispersed apatite is provided in a dispersed state. In one preferred embodiment the colloid-dispersed apatite is provided or fabricated by means of precipitation process. The colloid-dispersed apatite is provided as a raw material, in particular directly or indirectly taken from the fabrication. With respect to the fabrication of the colloid-dispersed apatite it is referred to the patent EP 0 938 449 B1. The content of this patent application is completely incorporated by reference.

The fabrication of the colloid-dispersed apatite is only described briefly: The constituents forming apatite and/or apatite molecules are provided dissolved or dispersed in a solution or suspension. By precipitation and in particular by a time-dependent agglomeration the colloid-dispersed apatite is formed or constituted. Generally, such a precipitated and preferably agglomerated colloid-dispersed apatite is a crystalline or nano-crystalline particle. For further fabrication details it is referred to the above stated incorporated patent application.

Said precipitated and/or precipitated and agglomerated colloid-dispersed apatite represents the above mentioned raw material. The solution or rather the dispersion of the colloid-dispersed apatite can be used directly in the present invention. The dispersion of the colloid-dispersed apatite can be diluted to the required concentration as well. Generally, the required colloid-dispersed apatite concentration has to be set for the dispersed system.

Also the apatite powder respectively its components are dispersed and not dissolved in the dispersed system. The apatite powder can be added to the dispersed system as being pulverized or as being part of another dispersed system. The powder is produced by drying the above mentioned fabricated raw material. By drying the dispersion respectively the precipitated and preferably agglomerated colloid-dispersed apatite, apatite solid matter or a kind of apatite solid matter is constituted or formed. The apatite powder can be provided by drying, preferably by spray-drying, the precipitated and/or the precipitated and agglomerated colloid dispersed apatite only. Since for instance the spray-drying results already in a pulverized or powdery state. Accordingly, in this variant the apatite powder according to the invention is provided by a dried material only.

In a further embodiment and in dependence on the drying process, by an optional or obligatory subsequent milling process and/or pulverizing process the apatite powder according to the invention is made. The powder particle size distribution can be adjusted by the used milling and/or pulverizing process. Preferably the powder particle size distribution is fabricated to the above mentioned powder particle size distribution. Accordingly, in this embodiment the apatite powder is provided by a dried and milled and/or pulverized material.

A large amount or high concentration of colloid-dispersed apatite seems to be necessary to achieve the deposition and/or formation of the apatite covering on the converted surface. Preferably, the colloid-dispersed apatite is provided in the dispersed system with a higher concentration than the apatite powder. Preferably the colloid-dispersed apatite is provided in the dispersed system with a concentration of 0.01 mg/l to 300 g/l, preferably 10 mg/l to 200 g/l, most preferably 0.1 g/l to 100 g/l. In particular the apatite powder is provided in the dispersed system with a concentration of 0.01 mg/l to 200 g/l, preferably 10 mg/l to 100 g/l, most preferably 0.1 g/l to 50 g/l.

The colloid-dispersed apatite and/or the apatite powder is respectively are at least one apatite selected from a group consisting of hydroxyl-apatite, flour-apatite and carbonate-apatite. Hydroxyl-apatite (HA) is the preferred embodiment of an apatite. HA improves osteoconduction. This enables a strong fixation of an implant inserted in a human body or in an animal body. It is assumed that an apatite, in particular HA, additionally retards or inhibits degradation. Further, an apatite, in particular HA, increases the bio-compatibility of an implant. Furthermore, the application of an apatite, in particular HA, results in a direct cell contact of the implant with osteoblasts.

The notation of pure HA is as following: $Ca_{10}(PO_4)_6(OH)_2$. The HA can be a substituted HA, in particular a multi-substituted HA, as well. Examples of substitution are as following:

the $Ca^{2+}$-sites of an apatite can be at least partially substituted by another constituent. Possible examples for the $Ca^{2+}$-constituent are $Sr^{2+}$, $Cd^{2+}$, $Mg^{2+}$, $Ba^{2+}$, $Pb^{2+}$, $Cu^{2+}$, $Zn^{2+}$, $Na^+$, $K^+$ and/or $Eu^{3+}$, the $OH^-$-sites of an apatite can be at least partially substituted by another constituent. Possible examples for the $OH^-$-constituent are $F^-$, $Cl^-$, $Br^-$, $I^-$, $S^{2-}$, $O^{2-}$ and/or $CO_3^{2-}$ and/or the $PO_4^{3-}$-sites of an apatite can be at least partially substituted by another constituent. Possible examples for the $PO_4^{3-}$-constituent are $SiO_4^{3-}$, $AsO_4^{3-}$, $SO_4^{3-}$, $MnO_4^{3-}$, $VO_4^{3-}$, $CrO_4^{3-}$, $CO_3^{2-}$ and/or $HPO_4^{2-}$.

For instance a HA-Si-compound is a so-called Si-substituted hydroxyl-apatite in which at least one $PO_4^3$ group is replaced by a $SiO_4^{3-}$ group. Such a HA-Si-compound is characterized by an enhanced bio-compatibility.

The dispersed system can be based on any kind of liquid. In one embodiment the dispersed system is provided as a water-based dispersion. Preferably the dispersion means are pure water or ion-exchanged water. The ph-value of the used water is less than or equal to 7.4. One example represents sterile water for irrigation.

Since neither the used colloid-dispersed apatite nor the apatite power is dissolved or comprises conductive particles, it is or can be necessary to provide conducting means in the dispersed system. Some possible examples for providing conductivity in the dispersed system represent dispersed metallic nano-particles and/or dissolved electrolytes. Conducting means also can be provided by an emulsifier which is required to provide a stable dispersed system. Also dissolved material, for instance of the immersed implant, can contribute to the conductivity in the dispersed system.

In a further embodiment of the present invention at least one additive is added to or provided in the dispersed system. Dependent on its property the additive is dissolved or dispersed in the dispersed system. Accordingly the additives are provided as electrolytes or as dispersed particles.

In one embodiment the added dispersed particles are provided as nano-particles. Said nano-particles generally have a mean average diameter of less than or equal to 100 nm, preferably less than or equal to 50 nm, most preferably less than or equal to 30 nm. Preferably the nano-particles, in particular the metallic nano-particles, are provided with a concentration of less than or equal to 100 mg/l.

In one embodiment of the invention the additive contributes to the conductivity in the dispersed system. Generally, an additive is chosen to be not harmful to the body but helpful for slow-down degradation and/or to avoid hydrogen gas release and/or accumulation.

One possible additive for the dispersed system is water glass which is added to or provided in the dispersed system. Possible examples for water glass are sodium water glass ($Na_2SiO_3$) and/or potassium water glass. Water glass reduces degradation and is effective in bone mineralization. Further, water glass enhances or promotes adhesion of the additives and/or the colloid-dispersed apatite and/or the apatite powder on the metallic surface. Furthermore, water glass promotes bonding between different minerals, added electrolytes and/or colloid-dispersed apatite and/or the apatite powder. The water glass can be provided in a liquid or as a liquid and therefore in a dissolved state. The water glass can be provided as a powder or in a solid state as well. Particularly the water glass is provided in the dispersed system with a concentration of 0.01 g/l to 400 g/l, preferably 0.01 g/l up to 200 g/l and most preferably 0.01 g/l to 50 g/l. The mostly preferred range is between 0.01 g/l to 15.0 g/l.

As an alternative or as a supplement at least one calcium containing compound and/or at least one phosphate containing compound is added to or provided in the dispersed system. These compounds promote the formation of apatite on the converted implant surface and/or the bonding of apatite to the converted implant surface.

As a further alternative or supplement at least one metal and/or at least one metal oxide and/or at least one metal hydroxide and/or at least one metal phosphate containing compound is provided in the dispersed system. The compounds and/or the constituents of the compounds are or can be embedded in the converted surface and/or deposited onto the converted surface and/or contribute to the constitution of apatite.

The metal, the metal of the metal oxide, the metal of the metal hydroxide and/or the metal of the metal phosphate containing compound is at least one metal which selected from a group consisting of at least one component of a material of the implant, sodium, potassium, magnesium, calcium, zinc, copper, silver, zirconium, aluminum, silicon and at least one component of the material of the implant.

With respect to the at least one component of the material of the implant: If the implant metal comprises magnesium, the additive is provided by magnesium. The metal additive is adapted to the substrate material (representing the implant). A contamination can be avoided.

It is expected that calcium and calcium phosphate compounds retard or inhibit degradation, increase bio-compatibility and contribute to the formation of an apatite covering. Typical examples represent calcium dihydrogenphosphate, dicalcium phosphate, amorphous calcium phosphate and/or β-TCP (tri-calcium-phosphate).

Some chosen additives, in particular the metal oxides or oxides in general, are believed to be a kind of scavenger. They are suitable to catch the released or evolved hydrogen gas which originates from degradation of the magnesium implant. Accordingly, gas bubble formation in the tissue can be at least reduced or avoided. Hydrogen gas evolution reduction can be such that the amount of hydrogen gas is resorbed or absorbed by the surrounding tissue. For instance calcium represents a calcium source for the formation or bonding of apatite. Silver, zinc and/or copper show an antibacterial effect.

Preferably the added metal oxide and/or the added metal hydroxide and/or the added metal phosphate containing compound is provided in the dispersed system with a concentration of less or equal to 20 g/l but larger than zero g/l. It is emphasized that above mentioned additives are exemplary and not restricted to this enumeration. The above mentioned concentrations relate to the concentrations in the dispersed system which is ready to be used for the PEO coating.

In a further embodiment a gas is provided in the dispersed system. The gas is for instance provided by a kind of bubbling. Particularly the gas is provided such to influence the PEO and/or to participate in the PEO. The gas comprises at least one type of gas selected from a group consisting of $N_2$, Ar, Kr and Xe. The mentioned noble gases are in particular suitable to achieve an enhanced densification of the converted layer.

The converted implant surface is uniformly covered with the oxide layer. Preferably the converted surface is continuously covered with the oxide layer. The thickness of the oxide layer is adapted to the application of the implant. In general the oxide film has a thickness of 0.1 μm to 100 μm, preferably 1 μm to 100 μm. A PEO converted surface according to one embodiment can be characterized by an enhanced roughness in comparison to a "simple" anodic oxidation process. Such a surface structure results in an implant surface of large specific surface area. For instance a rough surface is particularly advantageous for the ingrowth of tissue and a strong fixation of an implant in a body.

As already stated in the preceding description the colloid-dispersed apatite and/or the apatite powder are applied onto the surface of the implant when oxidizing the implant surface. A small fraction of apatite or its constituents also can be embedded in the oxide layer. The main fraction of the apatite is deposited onto the surface of the oxide layer and forms the continuous or non-continuous layer.

There exists no sharp interface between the oxide layer and the deposited or bonded apatite particle layer. The apatite particle concentration in the converted implant surface should be decreasing, preferably continuously decreasing, with increasing depth.

The apatite covering forms a coral-like structure on the converted surface. In dependence on the application of the implant the apatite covering can be provided as a partially covering on the converted implant surface or as a complete covering on the converted implant surface. An average thickness of an apatite covering should be in the range of 1 nm to 1000 nm. The apatite covering are provided by means of micro-arcs in the PEO process, for instance by implantation and/or deposition and/or agglomeration and/or constitution of the apatite powder and preferably also the colloid-dispersed apatite.

In one embodiment the apatite covering forms an island-like structure on the converted surface wherein the islands have an average area size of less than 3000 nm. The islands are surrounded by the oxide layer. Some islands also can be connected to each other. The island-like structure represents a non-continuous layer or film on the oxide film. Accordingly, the constituents Mg, MgO and the constituents of an apatite are directly "visible" respectively detectable on the surface.

The controlling of the covering amount of the apatite can be used to adjust or control its "effect". For instance the free or visible area of the oxide film of the converted surface can be adjusted. Both the degradation rate (corresponding to the bio-degradability of the implant) and the osteoconduction can be adjusted accordingly.

One parameter for the degradation rate represents the amount of hydrogen gas release or evolution. An implant according to the invention, preferably based on W4 magnesium alloy, is characterized by a hydrogen evolution rate of less than or equal to 1 ml/cm$^{-2}$day$^{-1}$. It is emphasized that the hydrogen gas evolution represents only one degradation process.

The degradation rate is determined by Electrochemical Impedance Spectroscopy (EIS). For example, one type of coated implant composed of W4-alloy is characterized by a degradation rate in terms of corrosion rate of less than or equal to 100 mpy, preferably of less than or equal to 60 mpy, most preferably of less than or equal to 20 mpy (mils per year). The listed degradation rate represents the initial degradation rate.

The AC voltage or alternating voltage is applied to the first electrode and/or the second electrode. The AC voltage is provided with a frequency of 0.01 Hz to 1200 Hz.

In a preferred embodiment the AC voltage is provided as an asymmetric AC voltage. The asymmetric AC voltage difference or asymmetric AC voltage represents an unbalanced AC voltage. This is an alternating voltage with different amplitudes to the negative and the positive components. It is emphasized that a pulsed DC voltage can be also interpreted as the AC voltage. The negative component is provided with amplitude ranging from −1200 V to −0.1 V. Preferably, the negative component is provided with amplitude ranging from −350 V to −0.1 V. In one embodiment, the negative component is provided with amplitude below −180 V or ranging from −350 V to −180 V. The positive component is provided with amplitude ranging from 0.1 V to 4800 V. Preferably, the positive component is provided with amplitude ranging from 0.1 V to 1400 V. In one embodiment, the positive component is provided with amplitude above +250 V or ranging from +250 V to 1400 V. In particular the quotient of the positive amplitude divided by the negative amplitude needs to be adjusted. The absolute value of the quotient ranges from larger 1 to 4.

In another embodiment the AC voltage is provided as a symmetric AC voltage. The negative component of the AC voltage is provided with amplitude ranging from −2400 V to −0.1 V. Preferably, the negative component is provided with amplitude ranging from −1200 V to −0.1 V. The positive component of the AC voltage is provided with amplitude ranging from +0.1 V to +2400 V. Preferably, the positive component is provided with amplitude ranging from 0.1 V to 1200 V.

A combination of both an asymmetric and a symmetric AC voltage is also possible. Such a voltage distribution is for instance suitable for a step-by-step-process or a multi-step-process for the fabrication of one coating. In a first step an asymmetric voltage or a symmetric voltage is applied to form the coating. In a further or second step, in particular after an interruption, the formation of the coating is continued by the application of a symmetric voltage or an asymmetric voltage respectively.

The voltage difference is provided with a magnitude which is sufficient for carrying out PEO. It is established an electric potential difference under plasma electrolytic conditions. The voltage is above a breakdown voltage of the oxide film growing on the surface of the implant. Preferably the maximum of the AC voltage difference is provided in the range of 0.1 V to 4800 V. Most preferably the maximum of the AC voltage difference is provided in the range of 100 V to 1400 V. In dependence on the conductivity of the dispersed system, the applied voltage difference results to a current density of 0.00001 to 500 A/dm$^2$, preferably of 0.00001 to 100 A/dm$^2$. Preferably, the applied voltage or voltage distribution is essentially constant or unchanged and the current density is adjusted during the PEO process.

A deposition rate in the range of 0.01 μm/s to 1 μm/s is achieved. Accordingly, with respect to the advantageous thickness of the oxide layer and/or the apatite islands a deposition time in the range of 1 s to 1500 s, preferred 1 s to 500 s, most preferred 20 s to 350 s, is achievable.

To enable a stable dispersion, the colloid-dispersed system is provided with a temperature of −20° C. to +150° C., preferably −20° C. to +100° C., most preferably between 0° C. to 75° C. The colloid-dispersed system is circulated with a circulation rate of 0 to 5000 liter/min, preferably 0.01 to 500 liter/min. This is for instance achieved by a mixer or mixing means or stirring means. As an optional supplement an emulsifying agent or emulsifier is provided in the dispersed system, in particular to avoid or to reduce an agglomeration of dispersed particles. A typical volume of the colloid-dispersed system is in the order of 0.001 liter to 500 liter, preferably 0.1 liter to 500 liter, most preferably 3 to 20 liter. Such volumes support an improved electrical field distribution in the dispersed system.

The implant according to the invention could be used in the field of traumatology, orthopaedic, spinal surgery and/or maxillofacial surgery. By means of a preferably surgical operation the implant is at least partially inserted or positioned in a human body and/or an animal body. The implant could be any kind of implant, preferably a surgical implant, which should not be removed in a further surgical operation. The implant could act as a preferably bone substitute as well.

Exemplary embodiments of such an implant according to the invention are plates, screws, nails, pins and/or at least partially internal fixation systems, rings, wires, clamps, blocks, cylinders and/or anchor items. It is emphasized that these applications are exemplary and not restricted to this enumeration.

The implant consists of metal or comprises metal. According to a first embodiment the implant is provided by a metal or by a metal alloy. According to a second embodiment the implant is provided by a composite or a composite material comprising a metal or a metal alloy. Such a composite or composite material contains metal or a metal alloy with an amount of at least 70 weight %.

The surface converted implants according to the invention base in a preferred embodiment on bio-compatible materials, preferably being bio-degradable. The material of a bio-degradable implant is magnesium or a magnesium-based alloy. The magnesium-based alloy contains at least 50 weight-% of magnesium, preferably at least 80 weight-% of magnesium, most preferably at least 90 weight-% of magnesium. An actually used alloy is the W4 Magnesium alloy (96% Magnesium, 4% Yttrium). Magnesium alloys were developed for orthopaedic applications. They have a Young modulus very close to that of natural bone and show excellent biocompatibility and bio-resorbability. The magnesium-based alloy is provided as a machined material, pressure casted material and/or die casted material. It is expected that the present invention is also suitable for further materials, in particular for metals preferably being non-bio-degradable, for instance to enhance bio-compatibility. In this embodiment the implant comprises at least one material selected from the group consisting of titanium, titanium alloys, chromium alloys, cobalt alloys and stainless steel. An alloy comprises at least 50 weight-% of the named main element. It is emphasized that above mentioned alloys and/or the fabrication methods are exemplary and not restricted to this enumeration.

In particular the implant according to the invention is producible, preferably is produced, with the method according to the invention. The implant comprises a surface composed of an oxide film which is partially or completely covered with an apatite covering.

The invention is explained subsequently in more detail on the basis of preferred embodiments and with reference to the appended figures. The features of the different embodiments are able to be combined with one another. Identical reference numerals in the figures denote identical or similar parts.

BRIEF DESCRIPTION OF THE DRAWINGS

It is shown in

In detail, it is shown in

Figure 2A:
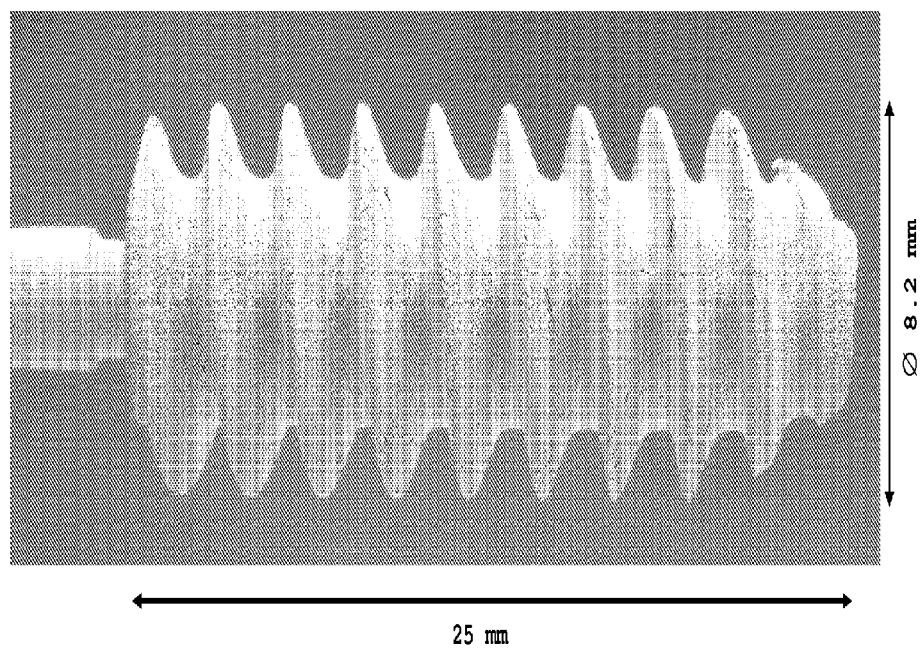
FIGS. 2a to 5b show results of a HA-MgO coating according to the invention which is applied onto a srew which is based on a magnesium alloy.
Figure 2B:
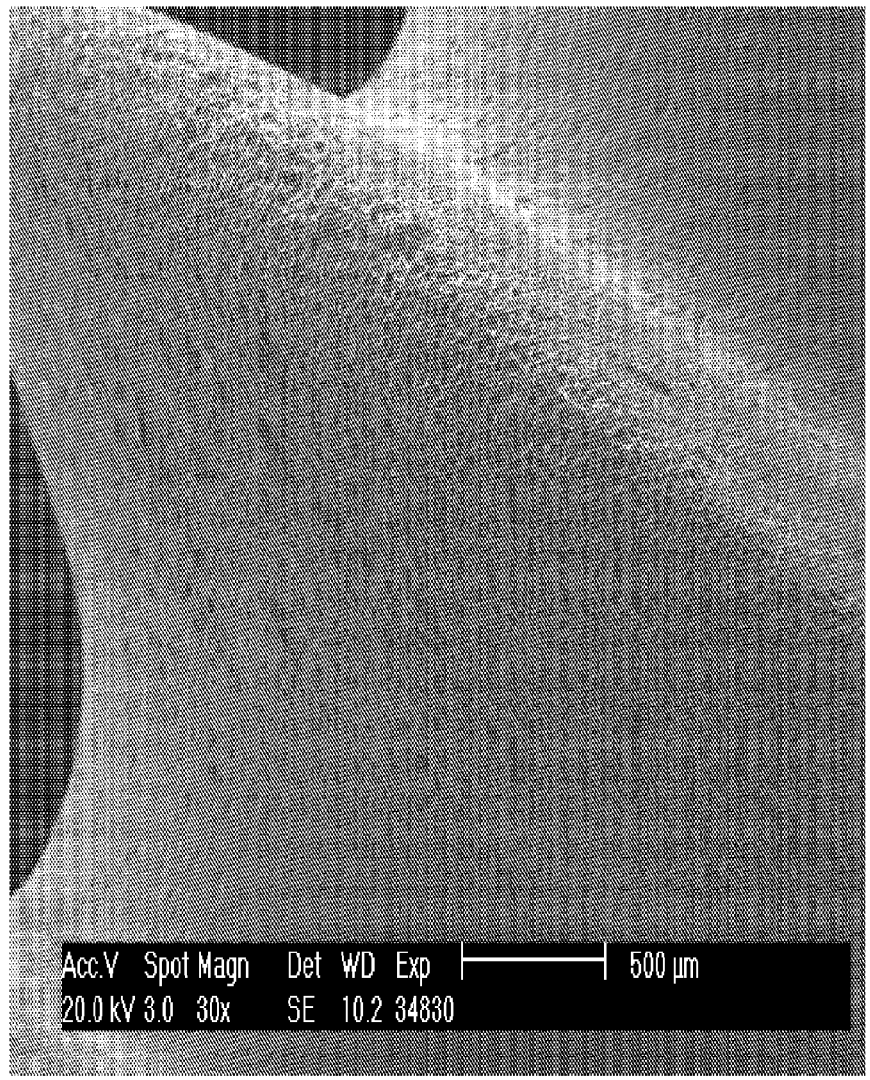
Figure 2C:
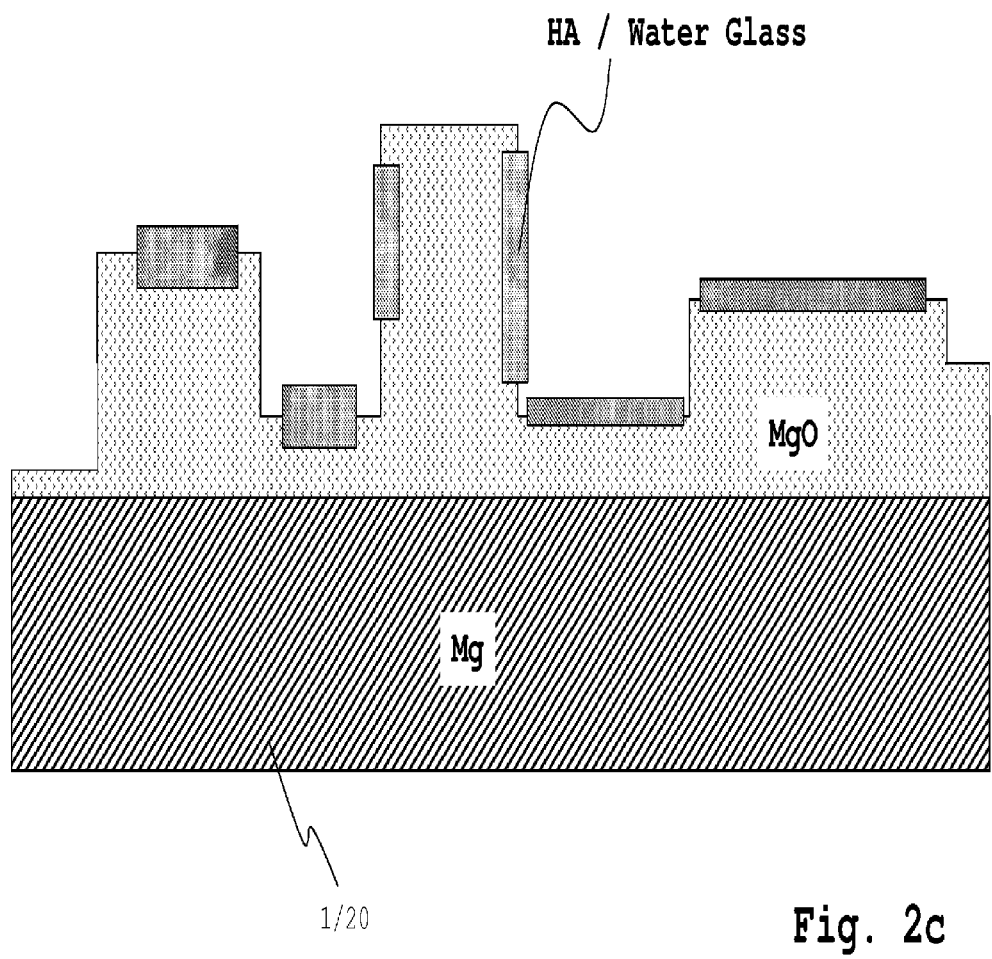
Figure 3A:
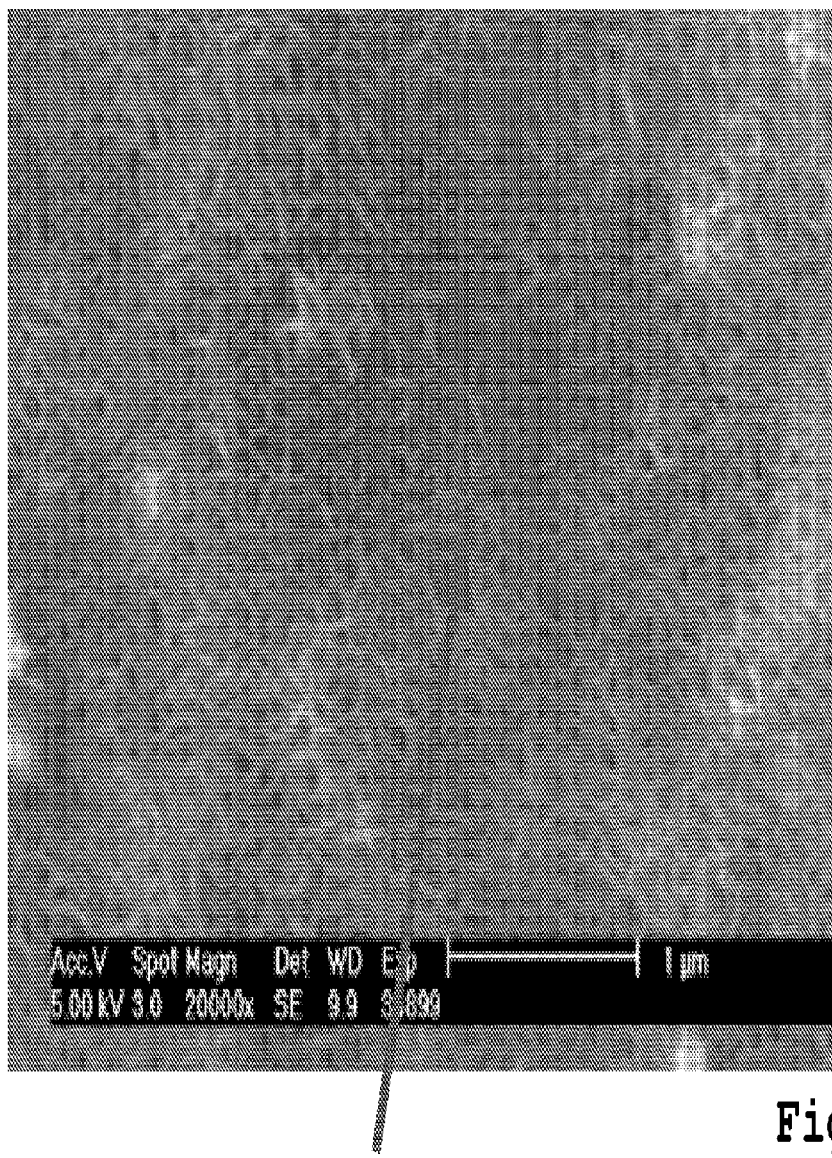
Figure 3B:
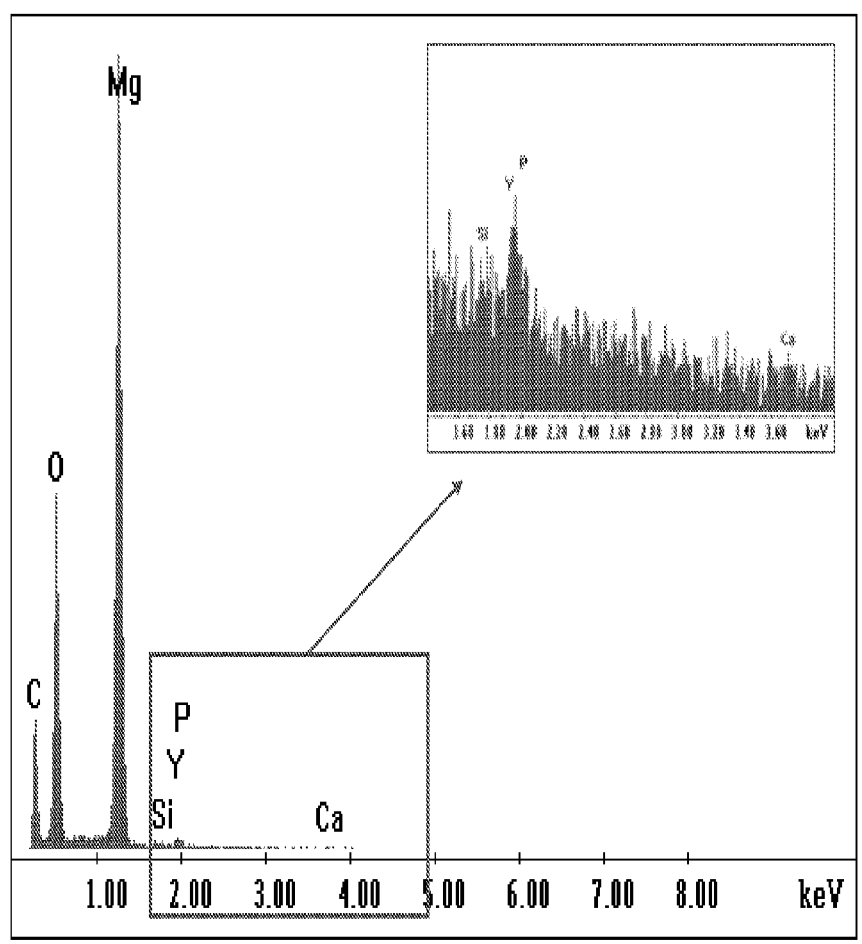
Figure 4A:
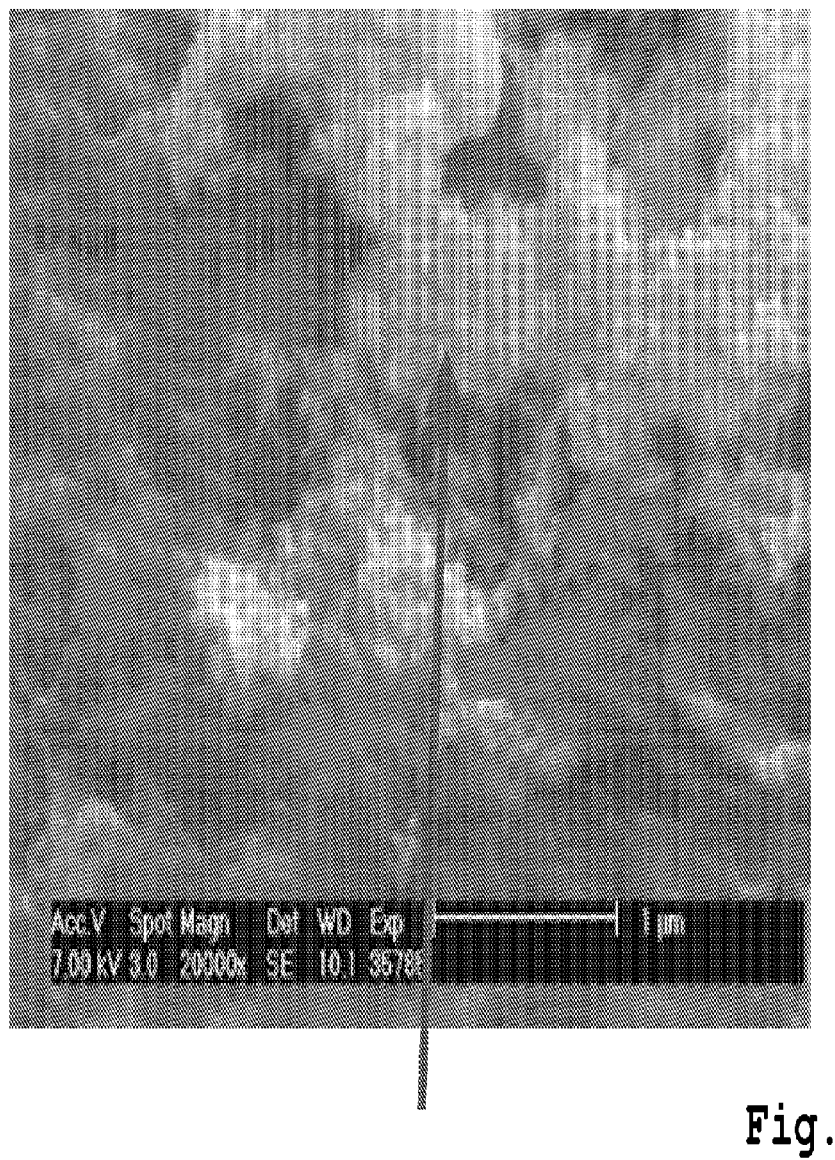
Figure 4B:
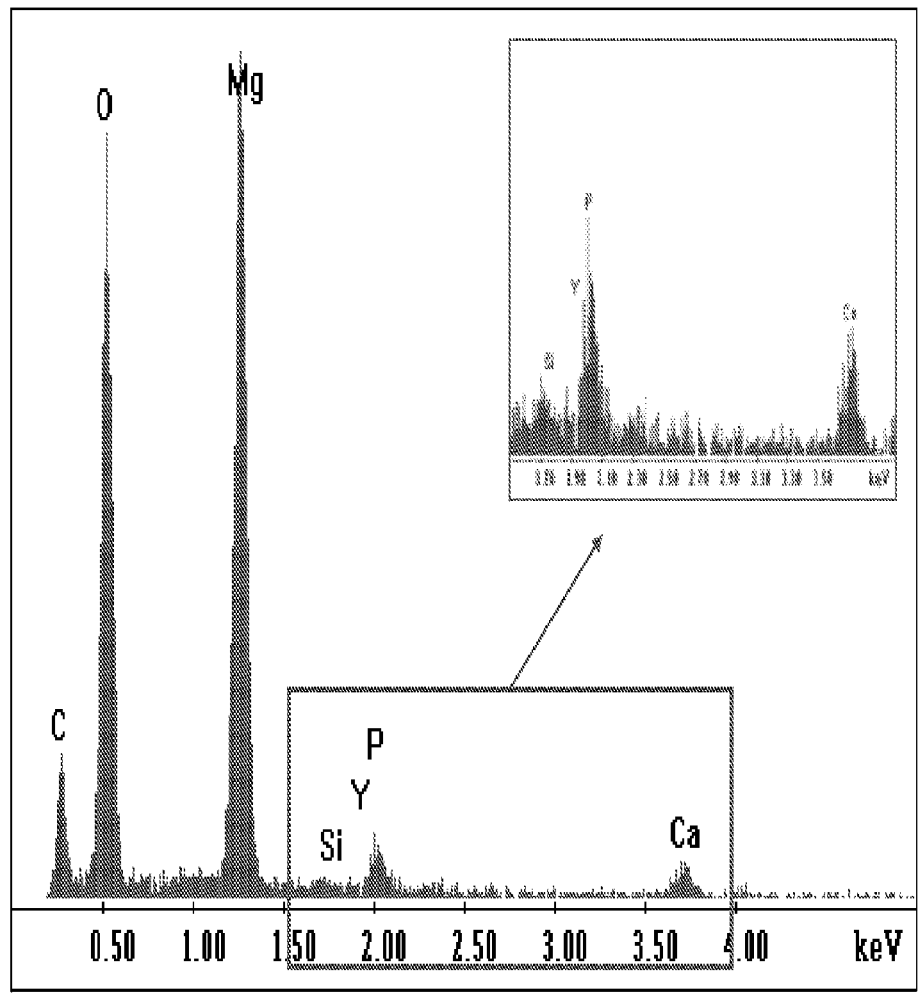
Figure 5A:
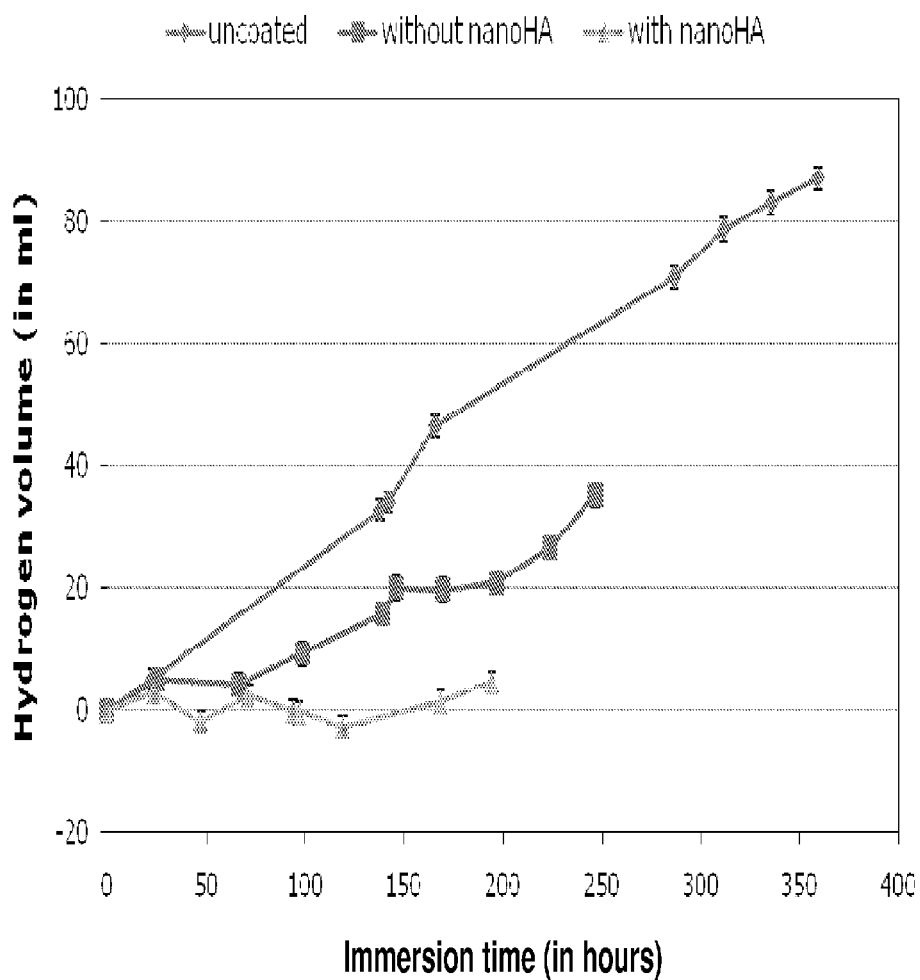
Figure 5B:
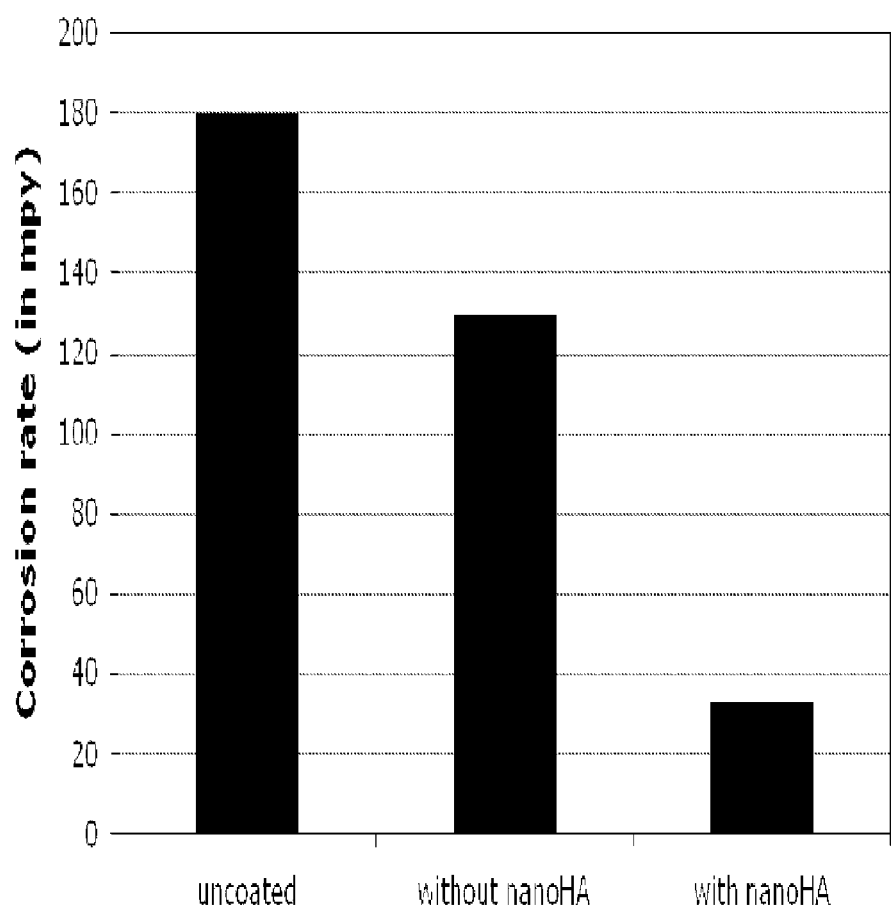

FIGS. 2a to 2c: images of the HA coating according to the invention using common photography (a), SEM in topography contrast mode (b) and a schematic cross sectional view of the converted surface (c), FIGS. 3a-b: an SEM image of the HA coating without nano-HA in chemical contrast mode (a), an EDX spectra of the bright region indicated by the tip of the arrow (b), FIGS. 4a-b: an SEM image of the HA coating with nano-HA in chemical contrast mode (a), an EDX spectra of the bright region indicated by the tip of the arrow (b), FIGS. 5a-b: the experimental results of immersion tests (a) and of electrochemical impedance spectroscopy (b) for an uncoated sample, a sample coated with nano-HA and sample coated without nano-HA.

Subsequently, preferred but exemplary embodiments of the invention are described in more detail with regard to the figures.

DETAILED DESCRIPTION OF THE INVENTION

FIG. 1 illustrates an apparatus for the fabrication of a coating according to the invention. The subsequent detailed description is directed to an implant. For instance for the coating of bio-degradable surgical implants the present innovative technique based on Plasma electrolytic oxidation (PEO) has been developed. PEO is an electrochemical surface treatment process for generating oxide coatings on metals. As a pulsed alternating current, with a high voltage, is passed through the dispersed system 4 or the electrolyte bath 4, a controlled plasma discharge is formed and sparks are generated on the substrate surface. This plasma discharge converts the surface of the metal into an oxide coating. The coating is in fact a chemical conversion of the substrate and grows both inwards and outwards from the original metal surface. Because it is a conversion coating, rather than a deposited coating (such as a coating formed by plasma spraying), it has excellent adhesion to the substrate metal.

The dispersed system 4 is provided in a bath 5. An implant 20 as a first electrode 1 is provided in the dispersed system 4. In the illustrated embodiment the implant 20 is completely immersed in the liquid 4 respectively the dispersed system 4. A second electrode 2 is provided as a cup also immersed or provided in the colloid-dispersed system 4. The second electrode 2 surrounds the first electrode 1.

The temperature of the dispersed system 4 is maintained or controlled by a heat exchanger 6 and/or a pumping system 7 and/or means for mixing 8. A circulation and/or mixing of the dispersed system 4 are achieved by the means for mixing 8. The means for mixing 8 are for instance provided by an acoustic hydrodynamic generator. As a possible and shown supplement a gas supply 9, for instance for air, can be also provided to the means for mixing 8. The circulation of the liquid can avoid or reduce an agglomeration of dispersed particles and/or can induce separation of agglomerated particles contained in the dispersed system 4.

In a further non-shown embodiment the second electrode 2 is provided by the bath 5 or the container 5 itself. This is for instance suitable for a container 5 which is provided by a conductive material. In such an embodiment the bath 5 and the second electrode 2 are provided as one-piece. In a preferred embodiment the first electrode 1 is approximately positioned in the center of the second electrode 2 in order to achieve an essentially uniform electrical field distribution.

Figure 1A:
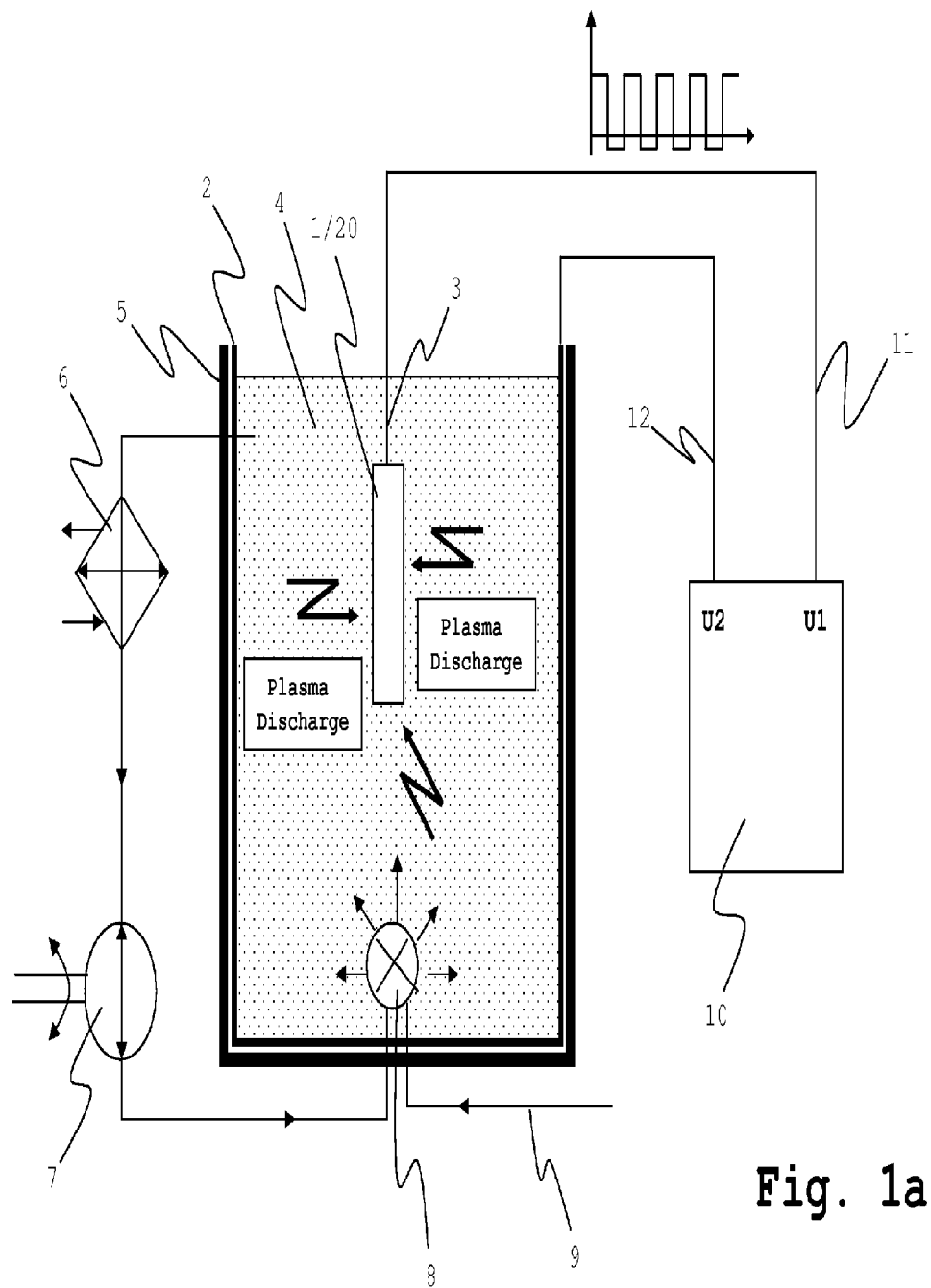
FIG. 1a schematically an apparatus for the fabrication of a coating according to the invention, FIG. 1b schematically a first embodiment of an asymmetric AC voltage distribution, FIG. 1c schematically a second embodiment of a symmetric AC voltage distribution, FIG. 1d schematically a third embodiment of an asymmetric AC voltage distribution combined with a symmetric AC voltage distribution
Figure 1B:
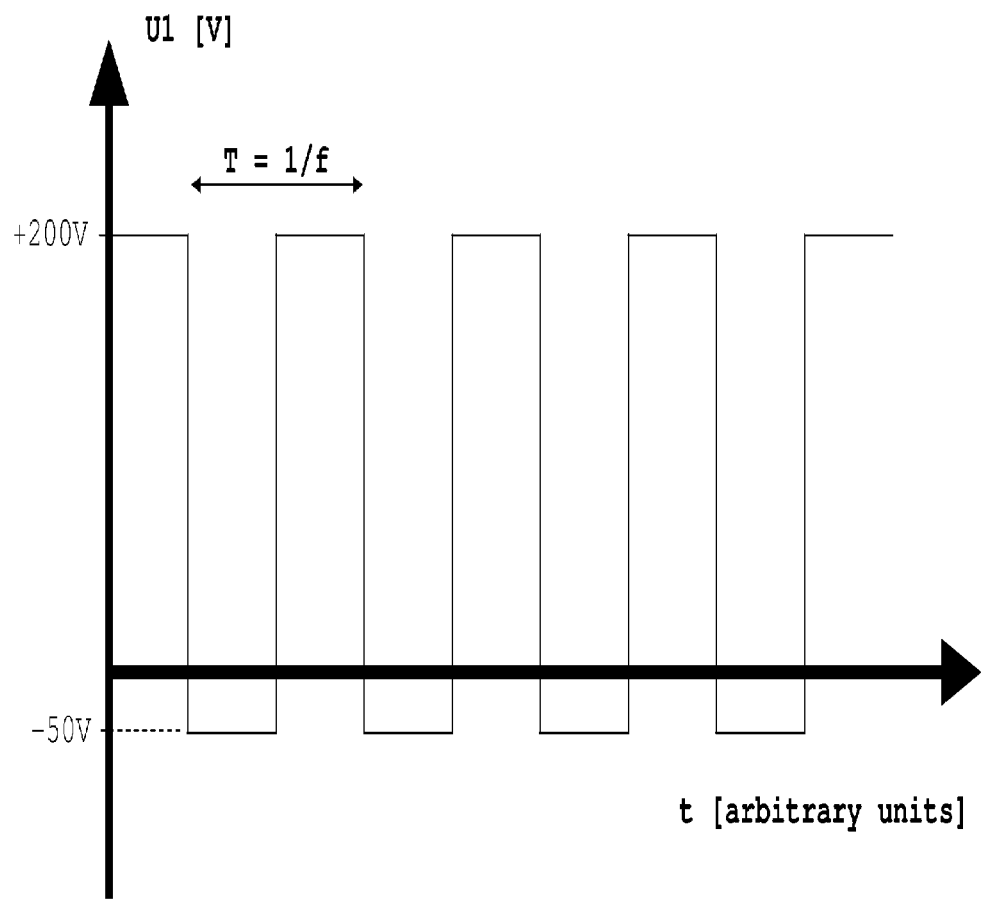
FIG. 1e shows a STEM image of nanoHA.

The AC voltage is provided by the power supply 10 (see FIG. 1a). The application of an asymmetric pulsed AC voltage results in a dense coating. The positive part of the pulse enables the growing of the converted surface. At the beginning of the oxide layer growing process the converted surface is characterized by a dense structure. With increasing oxide layer coating thickness the coating is getting more and more porous. The particles of the coating are getting more and more loosen. These loosen particles are removed in the negative part of the pulse. Accordingly, the negative part of the pulse is a so-called etching part. An asymmetric AC voltage is a voltage with different amplitudes to the positive and negative components. In particular the quotient of the positive amplitude divided by the negative amplitude needs to be adjusted. The absolute value of the quotient ranges from >1 to 4. For illustration purposes FIG. 1b schematically shows an asymmetric AC voltage distribution for amplitudes U1 of +200 V and −50V. These voltages are for instance applied to the implant 20 as the first electrode 1 (see FIG. 1a). In this embodiment the voltage of the second electrode 2 is for instance on ground potential. The shape is illustrated as being approximately rectangular-shaped. The shape can also be, in particular partially, a kind of a sinus or a sinus.

Figure 1C:
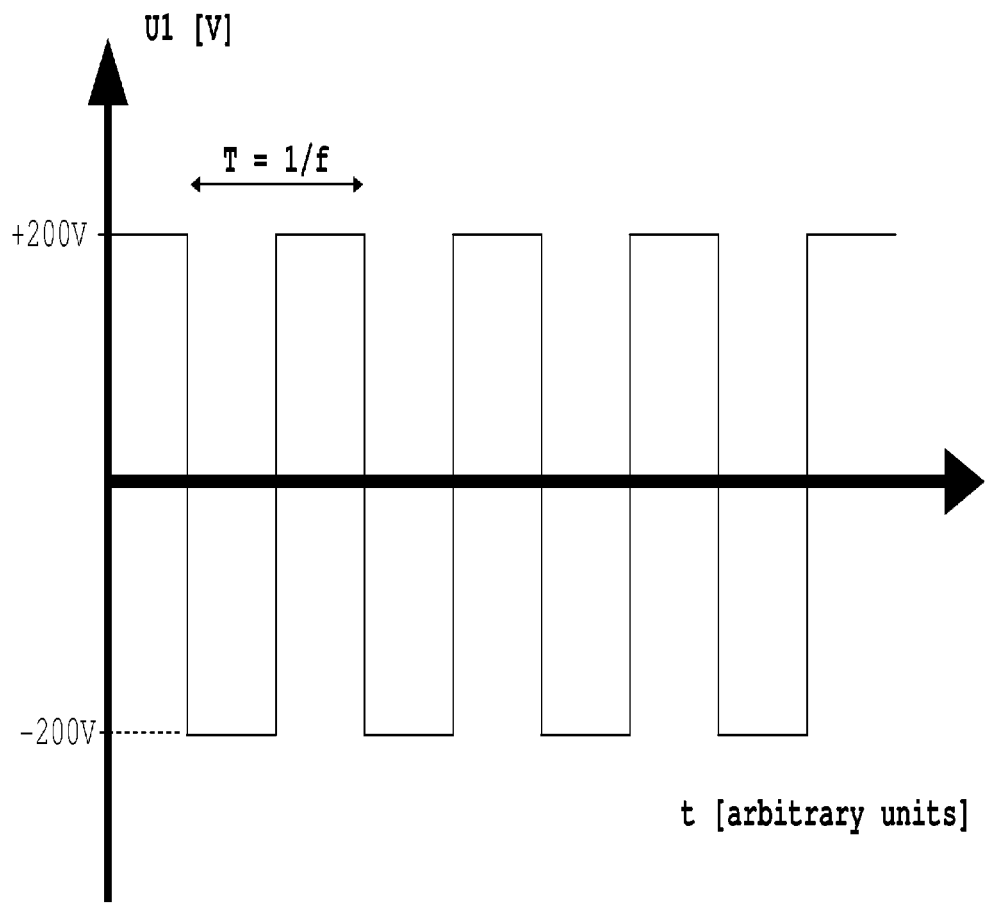

For some applications also a symmetric AC voltage distribution is suitable. One exemplary application is the obtaining of a coating with a very high surface roughness for improved implant-bone bonding. For illustration purposes FIG. 1c schematically shows a symmetric AC voltage distribution for amplitudes U1 of −200 V and +200V.

Figure 1D:
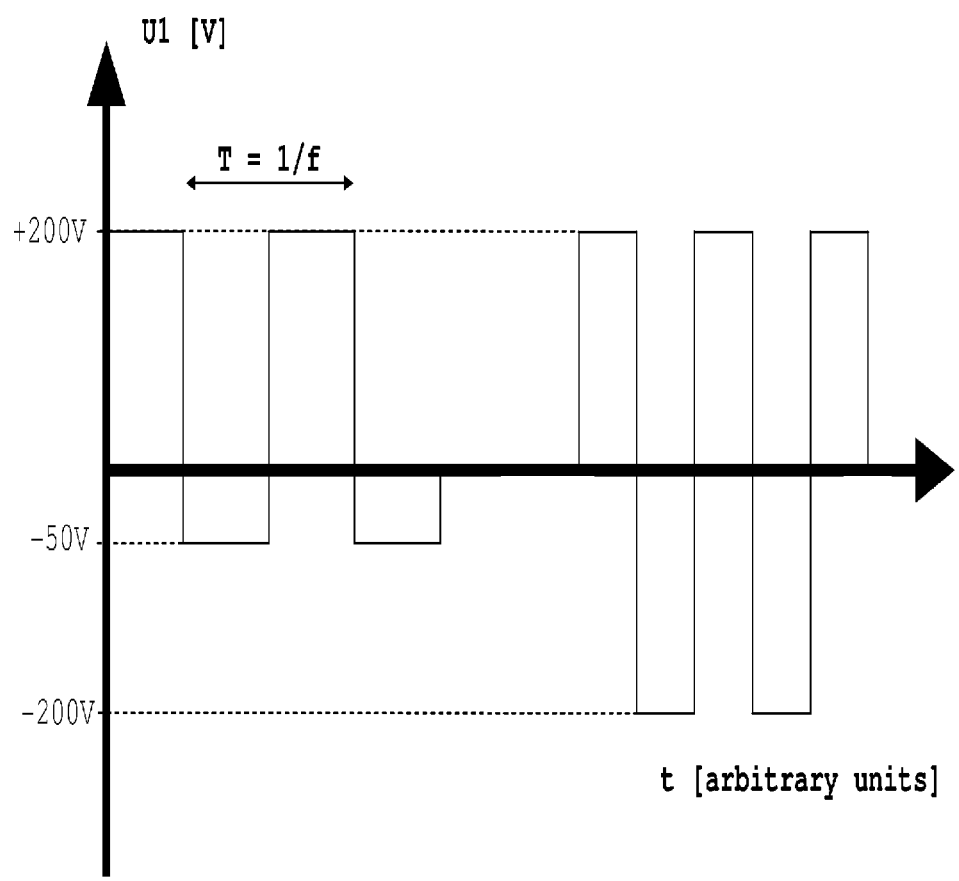

FIG. 1d shows a combination of both an asymmetric and a symmetric AC voltage. The shown voltages correspond to the voltages shown in FIGS. 1b and 1c. Only the period of the symmetric voltage is exemplary reduced. Such a voltage distribution is for instance suitable for a multi-step-process for the fabrication of one coating. In a first step an asymmetric voltage is applied to form a coating having a quite dense structure. In a second step, in particular after a break, the formation of the coating is continued by a symmetric voltage to obtain a surface having an enhanced surface roughness.

Figure 1E:

FIG. 1e shows a STEM image of colloid-dispersed apatite for the embodiment of HA. This colloid-dispersed apatite is also named as nanoHA. The shown nanoHA represents one embodiment for using in the present invention. As can be seen, the nanoHA has an elongated structure. The shown nanoHA is partially in an agglomerated state and partially in a non-agglomerated state. The size distribution of the nanoHA essentially depends on time. The nanoHA is present as non-agglomerated particles 30, as agglomerated particles or clusters of small size 31 and as agglomerated particles or clusters of larger size 32. The average length of non-agglomerated nanoHA is ranging up to 100 nm. The present agglomerated and the non-agglomerated nanoHA represents raw material.

The FIGS. 2a to 5b show experimental results of a HA-MgO coating according to the invention. Coating experiments were performed on die casted W4 magnesium interference screws (8.2×25 mm). Pressure casted and machined discs (18 mm, thickness 3 mm) of the same material were used for electrochemical impedance spectroscopy (see FIG. 5b) and for the immersion tests (see FIG. 5a).

First, FIG. 2a shows an image of the HA coating according to the invention using common photography. As an example a screw having a coating according to the invention is shown. The coating surface topography was investigated by stereo scanning electron microscopy (SEM) in topography contrast mode (FIG. 2b: topographical characterization according to ISO/TS 10993-19:2006). The images show a uniform and homogeneous coating of the surface with HA.

For illustration purposes FIG. 2c schematically shows a converted surface in a cross sectional view. The converted surface is continuously covered with the oxide layer and in this example only partially covered with HA. In this example the oxide film is characterized by hills and/or plateaus and/or craters separated by grooves and/or channels and/or ridges. However, the oxide film can be also flat. Particles of the dispersed system are also completely or partially included or embedded in the HA coating. Preferably the HA coating is formed by or built as a coral-like structure. As one example water glass and/or its constituents are included or embedded. On top of the oxide layer in this example a kind of apatite islands are developed forming a non-continuous layer of apatites. The islands can be formed on the plateaus and in the grooves.

FIGS. 3a to 4b show the results of a physico-chemical characterization (according to ISO/TS 10993-19:2006). In these figures the colloid-dispersed apatite is called as nanoHA. In detail FIGS. 3a-b show an SEM image of the HA coating in chemical contrast mode without or only a low amount of nano-HA (3a) and an EDX spectrum of the bright region indicated by the tip of the arrow (3b). FIGS. 4a-b show corresponding figures for the HA coating according to the invention with nano-HA.

The SEM image in chemical contrast mode clearly shows that there is no apatite or only a low amount of apatite or at least no detectable apatite on the surface of the sample which was treated in a dispersed system with an HA powder only but without nanoHA (see FIG. 3a). The applied concentrations in the composition correspond to the concentrations as mentioned below for the coating according to the invention (see FIGS. 4a and 4b) but without nanoHA. It is a net-like structure. The corresponding EDX spectrum confirms that there seems to be no or only few amounts of the elements calcium and phosphor, which are the main constituent elements of an apatite, on the PEO-formed oxide film of the converted surface. The oxide film is presented by the elements magnesium and oxygen.

This is in strong contrast to FIGS. 4a and 4b showing the results for a coating according to the invention. The SEM image in chemical contrast mode clearly shows the presence of a covering on the oxide film of the converted surface. This covering is provided by a coral-like structure or layer (see FIG. 4a). This covering can be also described as a kind of solidified foam. It is assumed that this coral-like structure is built or formed by HA or represents a partial or complete HA covering. The coral-like structure is related to HA crystals bonded together on the coating surface. The corresponding EDX spectrum confirms this assumption (see FIG. 4b). The elements calcium and phosphor being the main constituent elements of an apatite are present on the PEO-formed oxide film of the converted surface. Also the element silicon being one constituent of water glass is present in the spectrum. Accordingly, Ca—P—Si containing particles are found. The oxide film is presented by the elements magnesium and oxygen. Generally, the apatite or the coral-like structure owns an essentially elongated structure, for instance a cylindrical-like or rod-like structure. The presence of nanoHA in the dispersed system seems to be necessary for the formation of HA on the converted surface and/or for the deposition of HA onto the converted surface and/or the bonding of HA to the converted surface.

The applied concentration of the HA powder is 1.4 g/l. The applied concentration of the nanoHA is 1.6 g/l. Colloid-dispersed apatite particles with a particle size of about 15 nm to 60 nm and an apatite powder with a size distribution of 10 µm to 100 µm are very suitable. Additionally, the used dispersed system contains a concentration of 1.1 g/l water glass.

The purpose of an apatite-coating is the adaptation and/or the retardation of degradation, in particular the initial degradation. The initial degradation represents the occurring bio-degradation of a bio-degradable implant immediately or directly after implantation.

To illustrate the benefits of the present invention FIGS. 5a and 5b show the experimental results of immersion tests (a) and of electrochemical impedance spectroscopy (b). Also in these figures the colloid-dispersed apatite are called as nanoHA. The results are shown for an uncoated magnesium W4 sample, a magnesium W4 sample coated without nano-HA and a magnesium W4 sample having a coating according to the invention in which the coating is formed or established both by the nanoHA and by the HA powder.

FIG. 5a shows the entire acquired hydrogen volume which was evolved from the sample respectively produced in the sample-solution-interaction as a function of the immersion time. The hydrogen gas evolution measurement of magnesium is performed according to DIN 38 414. As expected the uncoated sample shows the highest hydrogen gas evolution because the magnesium is completely exposed to the test solution.

The degradation of the sample which is coated without the nanoHA is already reduced in comparison to the uncoated sample. This enhanced degradation resistance essentially origins from the PEO-formed oxide layer acting as a protection layer. The protecting oxide layer is gradually degraded by the test solution. Accordingly, the degradation increases with increasing immersion time.

The inventors surprisingly discovered that the degradation resistance can be tremendously enhanced by the combination of nanoHA and HA powder in the dispersed system. During the measured time spectrum essentially no hydrogen gas was evolved or formed respectively detected. This result proves the efficacy of the combination of nanoHA and HA powder in the dispersed system. It is expected that the constituted apatite covering or layer and the oxide coating will be gradually degraded in the end by the test solution also. After a particular time interval the sample or an implant inserted in a body will start to degrade as wanted. Accordingly, in a larger time scale this will result to an appearing and raising hydrogen gas evolution with increasing time. By controlling the apatite cover amount and/or the thickness of the oxide film and/or the porosity of the apatite coating and/or the porosity of the oxide layer the degradation characteristics of a bio-degradable implant based on magnesium can be adapted to the desired or required behavior, for instance the implant stability as a function of time.

FIG. 5b shows the results of Electrochemical Impedance Spectroscopy (EIS) measurements (according to ASTM G-106). In EIS a corroding metal could be modelized as an electrochemical system consisting of a double-layer capacitance ($C_{d1}$), a solution resistance and a charge transfer resistance (generally assimilated with the polarization resistance, $R_p$). Such a system can be studied by using an AC signal that can provide more information than a DC polarization. Thus, applying a 5 mV sinusoidal potential through a potentiostatic circuit, the potential-current response plots provide the impedance values. The impedance diagrams are recorded at the initial moment of time (t=0 h) immediately after the stabilization of the steady-state potential (about 5 to 20 min after immersion).

The Nyquist plots of the magnesium alloy at an open circuit exhibit two capacitive loops, one for high and intermediate frequencies and the other, the smaller one, for low frequencies. The first capacitive loop is attributed to the charge-transfer process. Thus, for the frequencies higher than 1 Hz, a resistor $R_p$ and a capacitor $C_{d1}$ in parallel can model the electrode/electrolyte interface. In some cases the second small capacitive loop is generally attributed to the mass transfer in the solid phase, which consists of the oxide/hydroxide layers.

The behavior of uncoated W4 in solutions imitating body's environments (0.9% NaCl solution stabilized with NaOH) was studied by electrochemical impedance spectroscopy (EIS). The purpose of this experiment was to compare the different composition in terms of degradation rate. The coating duration was the same for all compositions: 150 sec. During the experimental procedure 0.9% NaCl solution at body temperatures as well as an external pH control were used. The parameters were adjusted as follow: temperature of the solution—36.5-38.5° C., pH—7.35-7.45, flow rate of the solution between the reactor (500 ml) and the electrochemical cell (500 ml)—100 ml/min, speed of circulation of the solution inside of the electrochemical cell—300 ml/min. Measurements were taken using a potentiostat PARSTAT 2263 device (EG&G Princeton Applied Research) linked to a PC. Actually, the impedance diagrams were recorded exemplary at the initial time (t=0 h). The degradation rate at each time point can be deduced from the impedance diagram.

FIG. 5b shows the degradation rate in terms of corrosion rate for the initial time and therefore the initial degradation rate. The degradation rates of the two with apatite coated samples are all inferior to the degradation rate of the uncoated sample. Consequently the two formed coatings have a beneficial effect on the Mg-screws degradation.

However, the coated sample in which the coating was formed by both nanoHA and the HA powder shows a clearly reduced degradation rate both with respect to the uncoated sample and the coated sample without using nanoHA. The degradation rate, in particular the initial degradation rate is less than or equal to 20 mpy (mils per year).

Summarizing, it was shown that an HA-MgO coating according to the invention shows improved properties in terms of reduced hydrogen gas evolution, in particular reduced initial hydrogen gas evolution, and degradation resistance.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein. Accordingly, features of the above described specific embodiments can be combined with one another. Further, features described in the summary of the invention can be combined with one another. Furthermore, features of the above described specific embodiments and features described in the summary of the invention can be combined with one another.

What is claimed is:

1. An implant comprising a biodegradable magnesium-based alloy, having a treated surface wherein
the treated surface is at least partially converted to an oxide film by plasma electrolytic oxidation using a dispersed system comprising a colloid-dispersed apatite and
an apatite powder wherein
the converted surface is partially covered by apatite originating at least from the colloid-dispersed apatite and the apatite powder wherein
said biodegradable magnesium-based alloy has a treated surface with an oxide layer wherein
said oxide layer has an apatite covering wherein
the colloid-dispersed apatite has an average particle size of 100 nm or less
and wherein the apatite powder has an average particle size of 10 μm to 100 μm.

2. The implant according to claim 1, wherein the colloid-dispersed apatite or the apatite powder comprises hydroxyl-apatite or substituted hydroxyl-apatite.

3. The implant according to claim 1, wherein at least one metal oxide or at least one metal hydroxide or at least one metal phosphate containing compound is at least partially deposited onto the converted surface or embedded in converted surface.

4. The implant according to claim 3, wherein a metal of the metal oxide, a metal of the metal hydroxide or a metal of the metal phosphate containing compound is at least one metal selected from a group consisting of sodium, potassium, magnesium, calcium, zinc, copper, silver, zirconium, aluminum, silicon and at least one constituent of a material of the implant.

5. The implant according to claim 1, having a controlled degradation.

6. The implant according to claim 1 characterized by a hydrogen gas evolution rate of less than or equal to 1 ml/cm$^{-2}$day$^{-1}$ or a degradation rate of less than or equal to 100 mpy.

7. The implant according to claim 1, characterized in that said apatite powder is a precipitated and agglomerated colloid dispersed apatite.

8. The implant according to claim 1, characterized in that said oxide film has a thickness of 1 μm to 100 μm.

9. The implant according to claim 1, characterized in that said implant has an apatite covering with a thickness of 1 nm to 1000 nm.

10. The implant according to claim 1, characterized in that said implant has an apatite covering which forms a coral-like structure.

11. The implant according to claim 1, characterized in that said coral-like structure is formed from hydroxyl-apatite crystals which are bonded together.

12. The implant according to claim 1, characterized in that said implant has an apatite covering which forms an island-like structure on the converted surface.

13. The implant according to claim 12 characterized in that said islands have an average size of less than 3000 nm.

14. The implant according to claim 1, characterized in that said implant is embodied as a plate.

15. An implant being produced with a method for treating a surface of a bio-degradable metallic implant, said method comprising the following steps: providing a dispersed system comprising a colloid-dispersed apatite and adding an apatite powder to the dispersed system,
wherein the colloid-dispersed apatite is provided by precipitation and has an average particle size of 100 nm or less,
wherein the apatite powder has an average particle size of 20 μm to 100 μm,
subjecting an implant to the dispersed system such that a surface of the implant which is to be treated is immersed in the dispersed system,
applying an AC voltage difference between the implant as a first electrode and a second electrode positioned in the dispersed system for generating a plasma electrolytic oxidation on the immersed surface of the implant so that the immersed surface is converted to an oxide film which is at least partially covered by apatites formed at least by the colloid-dispersed apatite and the apatite powder, wherein a treated surface with an oxide layer which has an apatite covering is formed.

* * * * *